United States Patent [19]

Geiger et al.

[11] Patent Number: 4,696,913

[45] Date of Patent: Sep. 29, 1987

[54] NOVEL PEPTIDES WHICH ARE ACTIVE ON THE CENTRAL NERVOUS SYSTEM AND HAVE AN ACTION ON THE CHOLINERGIC SYSTEM

[75] Inventors: Rolf Geiger, Frankfurt am Main; Hermann Gerhards, Hofheim am Taunus; Hansjörg Kruse, Kelkheim, all of Fed. Rep. of Germany

[73] Assignee: Hoechst Aktiengesellschaft, Fed. Rep. of Germany

[21] Appl. No.: 902,615

[22] Filed: Sep. 2, 1986

Related U.S. Application Data

[62] Division of Ser. No. 663,193, Oct. 22, 1984, Pat. No. 4,623,715.

[51] Int. Cl.$^4$ .................. A61K 37/02; C07K 5/10; C07K 7/06
[52] U.S. Cl. .................. 514/15; 514/16; 514/17; 514/18; 530/328; 530/329; 530/330
[58] Field of Search .............. 530/330, 331, 329, 328; 514/15, 16, 17, 18

[56] References Cited

U.S. PATENT DOCUMENTS

| | | | |
|---|---|---|---|
| 3,842,064 | 10/1974 | Greven | 530/330 |
| 3,853,836 | 12/1974 | Greven | 530/330 |
| 3,853,838 | 12/1974 | Greven | 530/330 |
| 3,856,770 | 12/1974 | Greven | 530/330 |
| 4,104,371 | 8/1978 | Greven et al. | 530/329 |
| 4,491,579 | 1/1985 | Greven | 530/330 |

OTHER PUBLICATIONS

"Hoechst Informiert—Pharmakologische Perspektiven" pp. 61–75.

P. L. Wood et al., "Life Sciences," vol. 22 (1978) pp. 673–678.

P. L. Wood et al., "Journal of Pharmacology and Experimental Therapeutics," vol. 209 (1979), pp. 97–103.

L. J. Botticelli et al., "Brain Research", vol. 210 (1981) pp. 479–484.

L. J. Botticelli et al., "Journal of Neuroscience," vol. 2, No. 9 (1982) pp. 1316–1321.

Wied, "Annals of the New York Academy of Sciences," vol. 297 (1977) pp. 263–274.

Pigache, Psychopharmacology of Old Age (Ed. Wheatley), pp. 67–69, Oxford University Press, 1982.

Goldman, Bergman, "Peptides" 5 (1984) 1061–1065.

Strand, Kung, "Peptides 1" (1980) 135–138.

Report entitled "Enhancing Effects of a Synthetic ACTH(4–9)—Analogue on Different Learning Tasks in Mice and Rats, F. J. Hock, H. J. Gerhards, G. Wiemer and R. Geiger, Hoechst AG, D-6230 Frankfurt am Main 80, FRG.

Isaacson, Poplawsky, "Behavioral and Neural Biology", 39 (1983) pp. 52–59.

"Studies with Peptides Related to the Sequence 4–9 of ACTH," to be published in Proc. 19th Europ. Peptide Symposium De Gruyter, Berlin 1987.

"Behavioral and Neurochemical Effects of the Synthetic ACTH (4–9) Analoque HOE 427: An Approach to Therapy of Aging Disorders," Fourth Meeting of the International Study-Group on the Pharmacology of Memory Disorders Associated with Aging, Zurich, Switzerland, Jan. 16–18, 1987.

*Primary Examiner*—Delbert R. Phillips
*Attorney, Agent, or Firm*—Finnegan, Henderson, Farabow, Garrett & Dunner

[57] ABSTRACT

The invention relates to peptides of the formula I

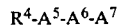

$$R^4\text{-}A^5\text{-}A^6\text{-}A^7 \qquad (I)$$

in which $R^4$ denotes an acyl group, $R^5$ denotes D-Lys or Lys, $A^6$ denotes the radical of phenylalanine, N-methylphenylalanine, 4-alkoxyphenylalanine or 1,2,3,4-tetrahydroisoquinoline-3-carboxylic acid, and $R^7$ denotes a basic radical, processes for their preparation and their use.

4 Claims, No Drawings

NOVEL PEPTIDES WHICH ARE ACTIVE ON THE CENTRAL NERVOUS SYSTEM AND HAVE AN ACTION ON THE CHOLINERGIC SYSTEM

This is a division of application Ser. No. 663,193, filed Oct. 22, 1984 U.S. Pat. No. 4,623,715.

We have observed that even simple dipeptide derivatives, such as, for example, $$Z\text{-Lys-Phe-OMe} \quad \text{(IV)}$$

(Z=benzyloxycarbonyl) cause the urge to groom and move in rats following intracerebroventricular (i.c.v.) administration of 10 μg. At the same time, cholinergic mechanisms in the central nervous system (CNS) are influenced. In the striatum of rats, the choline content is reduced and the acetylcholine content is increased following subcutaneous administration of 10 μg.

The effects are intensified if the carboxyl group carries a radical with basic substituents, it being possible for lysine to be in the D-form. Thus, for example, compound V $$Z\text{-D-Lys-Phe-NH-}(CH_2)_8\text{-NH}_2 \cdot 2HCl \quad \text{(V)}$$

already shows the same actions on i.c.v. or s.c. administration of 1 μg.

The effects described are characteristic of ACTH and MSH.

When the Z radical in V was replaced by phenylalanine and the α-amino group thereof was substituted by partial sequences of ACTH/MSH or by other acyl, aminoacid and peptide radicals, it was possible to observe a further increase in the effects in the cholinergic system, the urge to groom and move being weakened.

With the compounds of higher activity, not only an increased but also a reduced level of acetylcholine is observed. Both effects indicate an increased synthesis rate or an increased conversion.

An acceleration in the acetylcholine conversion in various areas of the brain following intracerebroventricular (i.c.v.) administration of alpha-MSH, ACTH and longer-chain ACTH fragments (ACTH 1–24) has already been described earlier by two study groups (P. Wood et al.: Life Sciences, 22 (1978), 673–678; JPET, 209 (1979), 97–103; L. J. Botticelli and R. J. Wurtmann: Brain Research 210 (1981), 479–484; and J. Neuroscience 2 (1982), 1316–1321).

ACTH-like short peptides which are known from Ann. N.Y. Acad. Sci. 297 (1977) 267–274 also have a neurotropic action.

In the abovementioned attempts to increase the action, it was found that the nature of the N-terminal substituents is less important than the substitution per se, especially when the substituents are peptides. The phenylalanines can also be modified without a loss in action. It was furthermore found that the C-terminal basic substituent always increases the action by about a 100-fold in comparison with an unsubstituted compound.

The invention thus relates to compounds of the general formula I $$R^4\text{-}A^5\text{-}A^6\text{-}A^7 \quad \text{(I)}$$

in which:
  $R^4$ denotes benzyloxycarbonyl (Z), ($C_2$–$C_6$)-alkanoyl, ($C_6$–$C_{10}$)-aryl-($C_2$–$C_4$)-alkanoyl or cycloalkanoyl with up to 2 alkyl and 5–7 cycloalkyl carbon atoms, bonded via $N_\alpha$, or
  $R^3$-$A^4$, in which
    $A^4$ represents the radical of a neutral aliphatic or aromatic α-aminoacid and
    $R^3$ represents hydrogen, Z, ($C_2$–$C_6$)-alkanoyl, ($C_6$–$C_{10}$)-aryl-($C_2$–$C_4$)-alkanoyl or cycloalkanoyl with up to 2 alkyl and 5–7 cycloalkyl carbon atoms, bonded via $N_\alpha$, or
  $R^2$-$A^3$-$A^4$, in which
    $A^4$ is as defined above,
    $A^3$ denotes His, Ala, Phe or D-Lys and
    $R^2$ is defined as $R^3$, or represents ($C_2$–$C_4$)-alkanoyl-ω-amino-($C_5$–$C_8$)-n-alkanoyl, methylsulfonyl-ω-amino-($C_5$–$C_8$)-n-alkanoyl, 4-methylsulfonylbenzoyl, succinoyl or glutaroyl, bonded via $N_\alpha$, or
  $R^1$-$A^2$-$A^3$-$A^4$, in which
    $A^3$ and $A^4$ are as defined above,
    $A^2$ represents pyroglutamyl, Glu, D-Glu or Ala and
    $R^1$ is defined as $R^2$, or represents ($C_2$–$C_4$)-alkanoyl-ω-amino-($C_3$–$C_4$)-n-alkanoyl, methylsulfonyl-ω-amino-($C_3$–$C_4$)-n-alkanoyl, methylamidoglutaroyl, H-Met, H-D-Met, H-Met(O), H-D-Met(O), H-Met($O_2$), H-D-Met($O_2$), H-Gly, Z-Gly, H-Tyr, Z-Tyr or pyroglutamyl, bonded via $N_\alpha$,
  $A^5$ denotes D-Lys or Lys,
  $A^6$ denotes the radical of phenylalanine, N-methylphenylalanine, 4-($C_1$–$C_4$)-alkoxyphenylalanine or 1,2,3,4-tetrahydroisoquinoline-3-carboxylic acid and
  $R^7$ denotes NH-$(CH_2)_n$-$NH_2$, Gly-NH-$(CH_2)_m$-$NH_2$, Gly-Lys-$R^8$ or Gly-D-Lys-$R^8$, in which n represents an integer from 4 to 10, m represents an integer from 2 to 6 and $R^8$ represents 1-pyrrolidinyl, 1-piperidinyl, NH-R or $NR_2$, where R=($C_1$–$C_4$)-alkyl, and physiologically acceptable salts thereof.

$R^4$ preferably denotes Z, phenyl-($C_2$–$C_4$)-alkanoyl, ($C_2$–$C_6$)-alkanoyl or $R^3$-$A^4$.

$A^4$ can denote, for example, the radical of an aliphatic aminoacid, such as Ala, Val, Leu, Ile or Met, of a substituted aliphatic aminoacid, such as Ser($C_1$–$C_6$-alkyl), Thr($C_1$–$C_6$-alkyl) or Cys($C_1$–$C_6$-alkyl), of an aromatic aminoacid, such as Phe or Phg (C-phenylglycine), or of a substituted aromatic aminoacid, such as Tyr($C_1$–$C_6$-alkyl). Advantageous radicals are those of, for example, Ala, Val, Leu, Ile, Phe, Tyr(Me) and Tyr(Et), in particular Phe, Ala and Leu, Phe being particularly preferred.

$R^3$ preferably represents hydrogen, Z, phenyl-($C_2$–$C_4$)-alkanoyl or ($C_2$–$C_6$)-alkanoyl.

$R^2$ preferably has the abovementioned meanings of $R^3$ or is acetyl-ε-aminocaproyl, methylsulfonyl-ε-aminocaproyl, 4-methylsulfonylbenzoyl or glutaroyl.

Preferred meanings of $R^1$ are the preferred meanings of $R^2$ and acetyl-β-alanyl, methylsulfonyl-β-alanyl, methylamidoglutaroyl, H-Met, H-Met(O), H-D-Met(O), H-Met($O_2$), H-Gly, Z-Gly, H-Tyr, Z-Tyr and pyroglutamyl, H-Met(O), H-Met($O_2$) and $HO_2C$-$(CH_3)_3CO$- are particularly preferred. The invention relates further to compounds with the R-configuration and to compounds with the S-configuration of the sulfinyl group of the radical H-Met(O)-.

$A^5$ is preferably D-Lys.

$A^6$ can denote, for example, the radical of phenylalanine, N-methylphenylalanine, 4-methoxyphenylalanine, 4-ethoxyphenylalanine or 1,2,3,4-tetrahydroisoquinoline-3-carboxylic acid, the L-configuration being preferred in each case; Phe is particularly preferred.

The nature of the basic C-terminal radical $R^7$ is not critical. Radicals such as -NH-$(CH_2)_n$-$NH_2$ have proved advantageous, n preferably being 6–10, in particular 8.

Some part sequences of preferred pentapeptide and hexapeptide derivatives are mentioned below: -Glu-His-Phe-D-Lys-Phe, -Ala-Ala-Phe-D-Lys-Phe- and -Glu-Ala-Phe-D-Lys-Phe-.

The following compounds of the formula I are particularly preferred: H-Met(O)-Glu-His-Phe-D-Lys-Phe-NH-$(CH_2)_8$-$NH_2$ and H-Met(O)-Glu-His-Phe-D-Lys-Phe-NH-$(CH_2)_6$-$NH_2$, in each case with the sulfonyl group in the S- or R-configuration, H-Met($O_2$)-Glu-His-Phe-D-Lys-Phe-NH-$(CH_2)_8$-$NH_2$, H-Met($O_2$)-Ala-Ala-Phe-D-Lys-Phe-NH-$(CH_2)_8$-$NH_2$ and HOOC-$(CH_2)_3$-CO-Glu-Ala-Phe-D-Lys-Phe-NH-$(CH_2)_8$-$NH_2$.

The invention furthermore relates to a process for the preparation of compounds of the formula I, which comprises condensing a fragment with an N-terminal free amino group with a fragment with a C-terminal free carboxyl group, the primary and secondary amino groups in these fragments which do not participate in the reaction being protected with a protective group of the urethane type which can be split off under acid conditions (such as, for example, Boc), and the carboxyl groups in these fragments which do not participate in the reaction being protected with protective groups of the ester type which can be split off under acid conditions (such as, for example, Bu$^t$), splitting off in the resulting compounds, under acid conditions, the protective groups introduced to protect amino or carboxyl groups, and, if appropriate, converting the compounds into their physiologically acceptable salts.

Protective groups of the urethane type are described in Schröder, Lübke, The Peptides, Vol. I, New York, London 1965, page 22 et seq., and those of the ester type are described in loc.cit., page 52 et seq.

The process is advantageously carried out by

| (a) condensing a compound of the formula IIa with a compound of the formula IIIa | |
|---|---|
| $R^4$—$A^5$—OH (IIa) | H—$A^6$—$R^7$ (IIIa) |
| (b) condensing a compound of the formula IIb with a compound of the formula IIIb | |
| $R^4$—OH (IIb) | H—$A^5$—$A^6$—$R^7$ (IIIb) |
| (c) condensing a compound of the formula IIc with a compound of the formula IIIc | |
| $R^3$—OH (IIc) | H—$A^4$—$A^5$—$A^6$—$R^7$ (IIIc) |
| (d) condensing a compound of the formula IId with a compound of the formula IIId | |
| $R^2$—OH (IId) | R—$A^3$—$A^4$—$A^5$—$A^6$—$R^7$ (IIId) |
| (e) condensing a compound of the formula IIe with a compound of the formula IIIe | |
| $R^1$—OH (IIe) | H—$A^2$—$A^3$—$A^4$—$A^5$—$A^6$—$R^7$ (IIIe) | in which the radicals $R^1$–$R^4$, $R^7$ and $A^2$–$A^6$ have the meanings defined in claim 1, but free primary and secondary amino groups, excluding the N-terminal groups of the compounds of the formulae IIIa–e, are protected with acid groups of the urethane type which can be split off under acid conditions, and free carboxyl groups, with the exception of the C-terminal groups of the compounds of the formulae IIa–e, are protected with protective groups of the ester type which can be split off under acid conditions, and then, in the compounds obtained according to (a)–(e), splitting off, under acid conditions, the protective groups introduced to protect the amino or carboxyl groups and, if appropriate, converting the resulting compounds into their physiologically acceptable salts. The reaction of compounds of the formula IIb with compounds of the formula IIIb is preferred.

The starting compounds of the formulae IIa–e and IIIa–e are known, or they are accessible in a manner which is known per se, for example by fragment condensation.

In the synthesis of the peptides according to the invention, the benzyloxycarbonyl or 9-fluorenylmethoxycarbonyl radical is preferred as the $N^\alpha$-protective group, and the tert.-butyl radical is preferred as the carboxyl-protective group.

The condensation in the process according to the invention is carried out by the general methods of peptide chemistry, in the case of sulfonyl compounds via the sulfonyl chloride, and otherwise preferably by the method of mixed anhydrides, via active esters or azides, or by the carbodiimide method, in particular with the addition of substances which accelerate the reaction and prevent racemization, such as, for example, 1-hydroxybenzotriazole, N-hydroxysuccinimide, 3-hydroxy-4-oxo-3,4-dihydro-1,2,3-benzotriazine and N-hydroxy-5-norbornene-2,3-dicarboximide, and furthermore using activated derivatives of 1-hydroxybenzotriazole or anhydrides of phosphoric, phosphonic and phosphinic acids.

Solvents are dimethylformamide, dimethylacetamide, hexamethylphosphoric acid triamide, N-methylpyrrolidone or dimethylsulfoxide. If the solubility of the components allows, solvents such as methylene chloride or chloroform can also be used. The methods mentioned are described, for example, in Meienhofer-Gross: "The Peptides", Academic Press, Vol. I, (1979).

The action of the compounds according to the invention on the cholinergic system is determined by a method described in J. Neurochem. 20 (1973), pages 1–8.

Some characteristic examples are listed in the following Table, which shows, inter alia, the increase in action of the peptides according to the invention containing basic substituents in comparison with ACTH and shorter unsubstituted peptides.

The compounds according to the invention effect a significant, dose-dependent weakening of the amnesia induced by electric shock or scopolamine in mice ("one-trial passive avoidance test"). For compound IX, for example, the minimum effective dose required is 0.03 μg/kg, following s.c. administration.

In humans, the peptides according to the invention have a mood-lightening, antidepressant and anxiolytic action. They increase attention to the environment, improve the learning and memory performance, have a favorable effect on resocialization processes and can be used for all diseases of post-traumatic and degenerative brain damage which are associated with a reduced central acetylcholine metabolism function, for example mild dementia and also early manifestations of Alzheimer's disease and the like.

The compounds according to the invention are used as medicaments in the form of their salts with physiologically acceptable acids, such as, for example, acetic acid, malonic acid, citric acid or malic acid, or as the hydrochloride or sulfate, if they are not present in the form of Zwitter ions. In the case of an adult of normal weight, intranasal administration is preferably effected in a dosage of 0.1 μg to 1 mg per dose, particularly preferably 1 to 500 μg and especially 5 to 200 μg per dose. The medicaments according to the invention can be administered, for example, up to 6 times, preferably up to 3 times, per day. In many cases, administration of one dose per day is also sufficient. The compounds according to the invention can also be administered subcutaneously in amounts of 0.001 to 10 μg/kg, preferably 0.01 to 5 μg/kg and in particular 0.05 to 2 μg/kg.

EXAMPLES

The abbreviations used in peptide chemistry are used in the following preparation examples.
Other frequently used abbreviations are:
DMF—dimethylformamide
NEM—N-ethylmorpholine
DCC—dicyclohexylcarbodiimide
DCU—dicyclohexylurea
DCA—dicyclohexylamine
HOBt—1-hydroxybenzotriazole
HOObt—3-hydroxy-4-oxo-3,4-dihydro-1,2,3-benzotriazine
Z—benzyloxycarbonyl

| Compound No. | Comparison substances: | Behavior (Grooming, yawning, stretching) (10 μg i.c.v.) | Biochemical effects in the striatum | | |
|---|---|---|---|---|---|
| | | | Dose mcg/kg s.c.; (rats) | ACH | CH |
| VI | ACTH-(1-24) | ++ | 0.01-1 | ↓ | ↑ |
| VII | Met—Glu—His—Phe—Arg—Trp—Gly—OH | φ | 10-1000 | ↑ | ↓ |
| VIII | Met(O)—Glu—His—Phe—D-Lys—Phe—OH | φ | 0.3-1 | ↑ | ↑ |
| IX | Met(O)—Glu—His—Phe—D-Lys—Phe—NH—$(CH_2)_8$—$NH_2$ | (+) | 0.01 | ↓ | ↓ |
| X | Met($O_2$)—Glu—His—Phe—D-Lys—Phe—NH—$(CH_2)_8$—$NH_2$ | φ | 0.01 | ↓ | ↓ |
| XI | H—Met($O_2$)—Ala—Ala—Phe—D-Lys—Phe—NH—$(CH_2)_8$—$NH_2$ | | 0.01 | ↑ | ↓ |
| XXII | HOOC—$(CH_2)_3$—CO—Glu—Ala—Phe—D-Lys—Phe—NH—$(CH_8)$—$NH_2$ | | 0.01 | ↑ | ↓ |
| XIII | H—Met($O_2$)—Glu—Ala—Phe—D-Lys—Phe—NH—$(CH_2)_8$—$NH_2$ | | 0.1 | ↑ | ↓ |
| XIV | H—Tyr—Glu—His—Phe—D-Lys—Phe—NH—$(CH_2)_3$—$NH_2$ | + | 0.1 | ↑ | ↓ |
| | Z—D-Lys—Phe—NH—$(CH_2)_3$—$NH_2$ | | 1.0 | ↑ | ↓ |
| XVI | pyro—Glu—Glu—His—Phe—D-Lys—Phe—NH—$(CH_2)_8$—$NH_2$ | | 0.1 | ↑ | ↓ |
| XIII | N—Met(O)—Glu—His—Phe—D-Lys—Phe—NH—$(CH_2)_6$—$NH_2$ | | 0.01 | ↓ | ↓ |

ACH = acetylcholine
CH = choline

Depending on their structure, they can be absorbed perorally to a greater or lesser degree. The comparatively wide dosage range for peroral administration is between 0.1 and 50 mg daily, divided over several administrations. The preferred individual dose for the compounds with the most potent action is 0.1 to 10 mg.

The compounds according to the invention can be administered orally or parenterally in a corresponding pharmaceutical formulation. For an oral use form, the active compounds are mixed with the additives usual for this purpose, such as excipients, stabilizers or inert diluents, and are brought into suitable forms of administration, such as tablets, coated tablets, push-fit capsules, aqueous alcoholic or oily suspensions or aqueous alcoholic solutions, by customary methods. Inert excipients which can be used are, for example, gum arabic, magnesium carbonate, potassium phosphate, lactose, glucose and starch, especially corn starch. The compounds can be formulated either as dry granules or moist granules. Examples of possible oily excipients or solvents are vegetable and animal oils, such as sunflower oil or cod liver oil.

For subcutaneous or intravenous administration, the active compounds or physiologically acceptable salts thereof are dissolved, suspended or emulsified, if desired with the substances customary for this purpose, such as solubilizing agents, emulsifiers or other auxiliaries. Examples of possible solvents for the novel active compounds and the corresponding physiologically acceptable salts are: water, physiological saline solutions and alcohols, for example ethanol, propanediol and glycerol, and in addition also sugar solutions, such as glucose or mannitol solutions, or a mixture of the various solvents mentioned.

Boc—tert.-butoxycarbonyl
Bu$^t$—tert.-butyl
Me—methyl
Et—ethyl
Tic—1,2,3,4-tetrahydroisoquinoline-3-carboxylic acid (L-form)
HONp—4-nitrophenol
HOTcp—2,4,5-trichlorophenol
HONSu—N-hydroxysuccinimide
TLC—Thin layer chromatography/thin layer chromatogram in the eluents:
 A: methyl ethyl ketone:pyridine-water-acetic acid (70:15:15:2)
 B: n-butanol:acetic acid:water (6:2:2)
 C: n-butanol:pyridine:acetic acid:water (4:1:1:5) from this the upper phase
 D: heptane:tert.-butanol:pyridine (3:1:1)

EXAMPLE 1

Z-D-Lys-Phe-NH-$(CH_2)_8$-$NH_2$.2HCl (a) Boc-NH-$(CH_2)_8$-NH-Boc 65 g of 1,8-diaminooctane are dissolved in 800 ml of dioxane and 400 ml of water. 69 ml of triethylamine are added, and 216 g of di-tert.-butyl dicarbonate are then added in portions at below 20° C., with vibromixing, the reaction product already precipitating. The mixture is subsequently stirred for 2 hours and the precipitate is filtered off, washed with a little water and dried. The filtrate is concentrated in vacuo, a precipitate being filtered off several times with suction and treated as above. The precipitates are collected, digested in water and dried.

Yield: 118 g of melting point 103°–104° C.

C18H36N2O4 (344.4).
Calculated: C 62.75, H 10.53, N 6.97. Found: C 63.0, H 10.7, N 7.2.

(b) Boc-NH-(CH2)8-NH2.HCl 68 g of the compound prepared according to (a) are suspended in 1 liter of dry ether containing 2N HCl. The suspension is stirred at room temperature for 3 hours and cooled to about 0° C. and the precipitate is filtered off and washed with dry ether.

Yield: 38 g, melting point: 150°-152° C. (decomposition).

C13H29ClN2O2 (280.8).

Calculated: 55.65, H 10.4, N 10.0, Cl 12.6. Found: C 55.6, H 10.5, N 10.2, Cl 12.5.

(c) Z-D-Lys(Boc)-Phe-OMe 43.2 g of Z-D-Lys(Boc)-OH, prepared analogously to the L-compound, are dissolved in 400 ml of dimethylformamide. 24.5 g of H-Phe-OMe.HCl, 15.33 g of HOBt, 14.53 ml of NEM and, with stirring, 25 g of DCC are added, and the mixture is left to stand overnight at room temperature. After the urea has been filtered off, the solvent is distilled off in vacuo and the oily residue is recrystallized from 200 ml of 80% strength ethanol.

Yield: 57.9 g (94% of theory).

For analysis, a sample is precipitated from DMF with ether/petroleum ether (1:1) and crystallized again from 80% strength ethanol.

C29H39N3O7 (541.6).

Calculated: C 64.31, H 7.26, N 7.76. Found: C 64.3, H 7.3, N 7.5.

$[\alpha]_D^{20} + 5.5°$ (c=0.5 in 90% strength acetic acid).

(d) Z-D-Lys(Boc)-Phe-OH 56.0 g of the methyl ester are dissolved in a mixture of 500 ml of dioxane, 200 ml of methanol and 60 ml of water, under the influence of heat, and are hydrolyzed at pH 12.5 with 1N NaOH in the course of 150 minutes. The pH is brought to 7 with 2N HCl, with stirring, most of the organic solvent is distiled off in vacuo, irrespective of the precipitate, 800 ml of ice-cold ethyl acetate are added, and 35 ml of 2N HCl are carefully added, with ice-cooling and vigorous stirring. The layers are separated and the ethyl acetate solution is washed with a little water, dried over sodium sulfate and concentrated in vacuo. After some time, the initially oily residue crystallizes completely and the crystals are washed with petroleum ether and dried in vacuo.

Yield: 50.2 g (92%). Melting point: 85°-87° C.

C28H37N3O7 (527.6).

Calculated: C 63.74, H 7.09, N 7.96. Found: C 63.3, H 7.3, N 8.4.

$[\alpha]_D^{20} + 10.7°$ (c=1 in 90% strength acetic acid).

(e) Z-D-Lys(Boc)-Phe-NH-(CH2)8-NH-Boc 48.5 g of the dipeptide prepared according to (d) and 25.8 g of the Boc-diamine hydrochloride prepared according to (b) are dissolved in 1 liter of DMF. 40.8 g of HOObt, 15 ml of NEM and, with cooling, 22.5 g of DCC are added in succession and the mixture is stirred for 1 hour and left to stand overnight at room temperature. The urea is filtered off, the solvent is distilled off in vacuo and the residue is recrystallized from 300 ml of 80% strength ethanol. The precipitate can be filtered off only with difficulty and is advantageously obtained by centrifugation.

Yield: 60.2 g (86.9%).

C41H62N5O8 (753.0).

Calculated: C 65.40, H 8.30, N 9.3. Found: C 65.6, H 8.5, N 9.3.

$[\alpha]_D^{20} + 2.0°$ (c=1 in 90% strength acetic acid).

(f) Z-D-Lys-Phe-NH-(CH2)8-NH2.2HCl 753 mg of the compound obtained according to (e) are left to stand in 7.5 ml of concentrated HCl/water/formic acid (0.6:0.6:9.6) for 30 minutes. The solvent is distilled off in vacuo and subsequent distillation with toluene is carried out. The residue solidifies on standing under ether, and is filtered off, washed with ether and dried in vacuo over KOH.

Yield: 650 mg.

In the TLC on silica gel in eluent A, the compound is a single compound.

The elementary analysis is within the limits of error.

EXAMPLE 2

Z-D-Lys-Phe-OMe.HCl

Analogously to Example 1f, the Boc group of 1.0 g of Z-D-Lys(Boc)-Phe-OMe, prepared according to Example 1c, is split off.

Yield: 820 mg, a single compound in the TLC (A), elementary analysis correct.

EXAMPLE 3

Z-Lys-Phe-NH-(CH2)8-NH2.2HCl

The Boc group of 1.2 g of the Boc-protected L-compound prepared analogously to Example 1e is split off as described above.

Yield: 0.98 g, single compound in the TLC (A), elementary analysis correct.

EXAMPLE 4

Z-Lys-Tic-NH-(CH2)8-NH2.2HCl

(a) Z-Lys (Boc)-Tic-OMe 15.2 g of Z-Lys(Boc)-OH and 9.1 g of H-Tic-OMe.HCl, prepared from the animoacid (J. Am. Chem. Soc. 70 (1948), page 182) with methanol/SOCl2 in a known manner, are reacted with 5.4 g of HOBt, 5.5 ml of NEM and 8.8 g of DCC in 300 ml of DMF analogously to Example 1e. The oil which remains after filtering off the urea and distilling off the DMF in vacuo is taken up in 200 ml of ethyl acetate and the solution is washed with 10% strength aqueous citric acid, 1M KHCO3 solution and water in succession, dried over Na2SO4 and evaporated in vacuo. The residue becomes foam-like on drying in vacuo, but does not crystallize.

Yield: 21.1 g.

(b) Z-Lys(Boc)-Tic-OH 17.9 g of the methyl ester prepared according to (a) are hydrolyzed analogously to Example 1. d After working up and distilling off the ethyl acetate, a non-crystallizing oil remains.

Yield: 15.9 g. A single compound in the TLC (A).

C29H37N3O7 (539.64).

Calculated: C 64.55, H 6.91, N 7.79. Found: C 63.9, H 6.9, N 7.9.

(c) Z-Lys(Boc)-Tic-NH-(CH2)8-NH-Boc 2.16 g of the compound described under (b) are reacted with 1.12 g of Boc-diamine hydrochloride, 0.54 g of HOBt, 0.7 ml of NEM an 0.9 g of DCC analogously to Example 1e. The crude product is taken up in ethyl acetate and washed analogously to (a). After the solvent has been distilled off, a non-crystallizing oily residue is obtained.

Yield: 2.73 g. A single compound in the TLC (A), apart from a trace of DCU.

(d) Z-Lys-Tic-NH-$(CH_2)_8$-$NH_2$.2 HCl

The Boc group is split off from 1.1 g of the compound prepared according to (c) in 10 ml of reagent according to Example 1f. The product is not crystalline. Yield: 0.61 g. Almost a single compound in the TLC (B, C).

EXAMPLE 5

Z-D-Lys-Tic-NH-$(CH_2)_8$-$NH_2$.2HCl

The compound is obtained analogously to Example 4. It is also not crystalline and is essentially a single compound in the TLC (B, C).

EXAMPLE 6

Z-Lys-Tic-OMe. HCl

Analogously to Example 1f, the Boc gorup is split off from 0.7 g of the compound obtained according to Example 4a. The residue is dissolved in water and the solution is filtered and freeze-dried. White powder. Yield: 0.43 g. Almost a single compound in the TLC (B, C).

EXAMPLE 7

Z-D-Lys-Phe-D-Lys-Phe-Gly-NH-$(CH_2)_4$-$NH_2$.3HCl (a) Z-D-Lys(Boc)-Phe-Gly-OME 1.26 g of G-Gly-OMe.HCl, 1.6 g of HOObt, 1.3 ml of NEM and 2.2 g of DCC are added in succession, with stirring, to 5.3 g of Z-D-Lys(Boc)-Phe-OH (Example 1d) in 60 ml of DMF. After the mixture has been left to stand overnight, the urea is filtered off and the filtrate is concentrated in vacuo. The residue is taken up in 200 ml of ethyl acetate and the solution is washed in the cold with 10% strength citric acid solution, saturated sodium bicarbonate solution and water and concentrated in vacuo to about 40 ml, and ether/petroleum ether 1:1 are added to the residue. The precipitate is filtered off, washed with ether/petroleum ether 1:1 and dried.

(b) H-D-Lys(Boc)-Phe-Gly-OME, TosOH 4.21 g of the compound obtained according to (a) are subjected to catalytic hydrogenation on Pd in 70 ml NeOH, with titration with 1N methanolic TosOH at pH 4.5. After the catalyst has been filtered off, the solvent is distilled off in vacuo and the residue is triturated several times with diisopropyl ether and dried.

Yield: 3.82 g, a single compound in the TLC (A, C).

(c) Z-D-Lys(Boc)-Phe-D-Lys(Boc)-Phe-Gly-OMe 1.6 g of HOOBt, 1.3 g of NEM and 2.2 g of DCC are added to 5.3 g of Z-D-Lys(Boc)-Phe-OH and 6.4 g of H-D-Lys(Boc)-Phe-Gly-OMe, TosOH in 100 ml of DMF, with stirring. After the mixture has been left to stand overnight and the urea has been filtered off, the solvent is distilled off in vacuo. The residue is taken up in 300 ml of ethyl acetate/n-butanol (2:1), the mixture is washed, as above, with citric acid solution, sodium bicarbonate solution and water and dried over sodium sulfate and the solvent is distilled off in vacuo. The residue is recrystallized from 60 ml of isopropanol.

Yield: 7.0 g, a single compound in the TLC (A).

(d) Z-D-Lys(Boc)-Phe-D-Lys(Boc)-Phe-Gly-OH 5.4 g of the methyl ester are dissolved in 50 ml of dioxane + 50 ml of methanol + 20 ml of water, under the influence of heat, and are hydrolyzed at pH 13 with 1N NaOH. The pH is brought to 6 with 2N HCl in the cold, most of the solvent is distilled off, 100 ml of ethyl acetate and 20 ml of n-butanol are added and the mixture is acidified to pH 2 in the cold with 1N HCl and washed with water. The organic phase is dried over sodium sulfate and evaporated in vacuo. The oily residue solidifies on trituration with ether.

Yield: 5.1 g, almost a single compound in the TLC (A).

(e) Z-D-Lys(Boc)-Phe-D-Lys(Boc)-Phe-Gly-NH-$(CH_2)_4$-NH-Boc 0.44 g of Boc-NH-$(CH_2)_4$-$NH_2$.HCl, prepared according to Liebig's Ann. Chem. 750 (1971) 165, are added to 1.9 g of the compound obtained according to (d) in 30 ml of DMF, followed by 0.27 g of HOBt, 0.3 ml of NEM and 0.45 g of DCC, with stirring. After the mixture has been left to stand overnight, the urea has been filtered off and the DMF has been distilled off in vacuo, the residue is taken up in 60 ml of ethyl acetate/n-butanol (1:1) and the mixture is washed, as above, with citric acid solution, bicarbonate solution and water, dried and freed from the solvent in vacuo. The residue is recrystallized from isopropanol.

Yield: 1.55 g, a single compound in the TLC (A, C).

(f) Z-D-Lys-Phe-D-Lys-Phe-Gly-NH-$(C_2)_4$-$NH_2$.3HCl 582 mg are dissolved in 5.4 ml of HCl/HCOOH analogously to Example 1f and the mixture is worked up as in that example.

Yield: 440 mg, a single compound in the TLC (B, C).

EXAMPLE 8

H-Phe-D-Lys-Phe-NH-$(CH_2)_8$-$NH_2$.3HCl (a) Z-Phe-D-Lys(Boc)-Phe-NH-$(CH_2)_8$-NH-Boc 10.8 g of H-D-Lys(Boc)-Phe-NH-$(CH_2)_8$-NH-Boc. TosOH, prepared from the Z-compound analogously to Example 7b by catalytic hydrogenation in methanol at pH 4.5, with titration with 1N TosOH, are dissolved in 100 ml of DMF, and 4.1 g of Z-Phe-OH, 1.8 g of HOBt, 2 ml of NEM and 3.0 g of DCC are added in succession, with stirring. After the mixture has been left to stand overnight, the urea is filtered off and the DMF is distilled off in vacuo. The residue is recrystallized from 50 ml of 80% strength ethanol.

Yield: 8.2 g, a single compound in the TLC (A).
$C_{50}H_{71}N_6O_9$ (900.2).
Calculated: C 66.72, H 7.95, N 9.34. Found: C 66.7, H 7.9, N 9.1.
$[\alpha]_D^{20}$: +3.0° (c=1 in 90% strength acetic acid).

(b) H-Phe-D-Lys(Boc)-Phe-NH-$(CH_2)_8$-$NH_2$.HCl 1.0 g of the compound obtained according to (a) is catalytically hydrogenated analogously to Example 7b, but the pH is maintained with 1N HCl in methanol. After analogous working up, 0.92 g of product which is a single compound in the TLC (D) is obtained.

(c) H-Phe-D-Lys-Phe-NH-$(CH_2)_8$-$NH_2$.3HCl

Splitting off of the Boc protective groups from the compound obtained according to (b) as in Example 1f.

Yield: 0.86 g, almost a single compound in the TLC (A, B). Aminoacid analysis: Phe:Lys (2.0:1.04).

EXAMPLE 9

Z-Glu-His-Phe-D-Lys-NH-$(CH_2)_8$-$NH_2$.2HCl (a)

H-Phe-D-Lys(Boc)-Phe-NH-$(CH_2)_8$-NH-Boc.TosOH 7.5 g of the Z-compound prepared according to Example 8a are catalytically hydrogenated in methanol and the mixture is worked up, analogously to Example 7b.

Yield: 7.3 g, a single compound in the TLC (D).

(b)

Z-Glu(OBu$^t$)-His-Phe-D-Lys(Boc)-Phe-NH-$(CH_2)_8$-NH-Boc 5.16 g of the compound obtained according to (e) in 70 ml of DMF are reacted with 2.76 g of Z-Glu(OBu$^t$)-His-OH, 0.9 g of HOObt, 0.7 ml of NEM and 1.22 g of DCC and the mixture is worked up analogously to Example 4a. The residue which remains after the ethyl acetate has been distilled off is triturated several times with ether/petroleum ether (1:1) and dried.

Yield: 5.0 g. According to the TLC (A, C), contaminated with only a very little DCU.

(c) Z-Glu-His-Phe-D-Lys-Phe-NH-$(CH_2)_8$-$NH_2$.2HCl

Analogously to Example 1f, the Boc and Bu$^t$ protective groups are split off from 0.5 g of the compound obtained according to (b), and the mixture is worked up as described in that example. The product is then dissolved again in a little water, the solution is stirred with a little weakly basic ion exchanger to pH 4.5 and filtered and the filtrate is evaporated to dryness in vacuo. The residue is triturated with ether and dried. Yield: 0.3 g, almost a single compound in the TLC (A, B). Aminoacid analysis correct.

EXAMPLE 10

Phenylpropionyl-Glu-His-Phe-D-Lys-Phe-NH-$(CH_2)_8NH_2$.3$CH_3$COOH

Z is split off by catalytic hydrogenation from the Z-peptide prepared according to Example 9b. The product is reacted with phenylpropionic acid, DCC and HOBt in a molar ratio and the Boc and tert.-butyl groups are split off from the reaction product with HCl/HCOOH. After the product has been converted into the acetate analogously to Example 1G, the acetate is purified by chromatography on Sephadex$^{(R)}$ LH 20, as described in that example.

A single compound in the TLC (A, B, C). Aminoacid, analysis correct.

EXAMPLE 11

H-Met(O)-Glu-His-Phe-D-Lys-Phe-NH-$(CH_2)_8$-$NH_2$.3$CH_3$COOH (a)

Boc-Met-Glu(OBu$^t$)-His-Phe-D-Lys(Boc)-Phe-NH-$(CH_2)_8$-NH-Boc

Analogously to Example 7b, 4.2 g of H-Glu(OBu$^t$)-His-Phe-D-Lys(Boc)-Phe-NH-$(CH_2)_8$-NH-Boc. TosOH are prepared from 3.75 g of the compound obtained according to Example 9b. 2.56 g of the product in 60 ml of DMF are reacted with 1.2 g of Boc-Met-ONp, 27 mg of HOBt and 0.4 ml of NEM overnight at room temperature, the solvent is distilled off in vacuo and, after digestion with $NaHCO_3$ and water, the residue is reprecipitated from ethyl acetate/ether, digested with ether and dried.

Yield: 2.2 g, a single compound in the TLC (C).

(b)

Boc-Met(O)-Glu(OBu$^t$)-His-Phe-D-Lys(Boc)-Phe-NH-$(CH_2)_8$-NH-Boc 1.8 g of the compound obtained according to (a) are oxidized with 2 ml of 3% strength $H_2O_2$ in 36 ml of acetic acid. After 30 minutes, the mixture is concentrated in vacuo and the residue is digested with water and ether.

(c)

H-Met(O)-Glu-His-Phe-D-Lys-Phe-NH-$(CH_2)_8$-$NH_2$.3$CH_3$COOH

Analogously to Example 1f, the crude product obtained according to (b) is freed from the protective groups with 25 ml of HCl/HCOOH. The mixture is evaporated to dryness in vacuo, the residue is dissolved in 30 ml of 50% strength methanol and the solution is treated with the ion exchanger Amberlite ® IRA 93 in the acetate form, until the pH value has returned to about 4.2, filtered and evaporated to dryness in vacuo.

Yield: 1.36 g.

For purification, the product is dissolved in 6 ml of 1% strength acetic acid and chromatographed in the same solvent over a 200×2.5 cm column of Sephadex ® LH-20. 480 mg of a chromatographically single peptide with a correct aminoacid analysis are found in fractions 5 and 6.

$[\alpha]_D^{20}$: +4.9° (c=0.5 in 90% strength acetic acid).

290 g of a mixture with the stereoisometric Met(O) derivative are found in fraction 7.

EXAMPLE 12

H-D-Met(O)-Glu-His-Phe-D-Lys-Phe-NH-$(CH_2)_8$-$NH_2$.3$CH_3$COCH

The procedure is analogous to Example 11, but Boc-D-Met-ONp is used and the title compound is obtained in corresponding purity after chromatography on Sephadex ® LH-20.

EXAMPLE 13 pGlu-Glu-His-Phe-D-Lys-Phe-NH-$(CH_2)_8$-$NH_2$.2$CH_3$COOH (a)

pGlu-Glu(OBu$^t$)-His-Phe-D-Lys-(Boc)-Phe-NH-$(CH_2)_8$-NH-Boc 1.6 of H-Glu(OBu$^t$)-His-Phe-D-Lys-Phe-NH-$(CH_s)_8$-NH-Boc. TosOH (Example 11a) and 370 mg of pGlu-OTcp are reacted in 20 ml of DMF in the presence of 0.17 ml of NEM and 17 mg of HOBt overnight. The solvent is distilled off in vacuo and the residue is digested with ether.

Yield: 1.6 g.

(b) The crude product obtained under (a) is freed from the protective groups analogously to Example 1f, and the product is purified by chromatography analogously to Example 11c. 465 mg of the title compound, which is a single compound in the TLC (C), are obtained. Aminoacid analysis correct.

EXAMPLE 14

Z-Tyr-Glu-His-Phe-D-Lys-Phe-NH-(CH$_2$)$_8$-NH$_2$.2CH$_3$COOH 1.28 g of the partly protected pentapeptide-amide described in Example 11a are reacted in 20 ml of DMF with 610 mg of Z-Tyr(Bu$^t$)-ONSu in the presence of 13.5 mg of HOBt and 0.13 ml of NEM. After the mixture has been left to stand overnight, the solvent is distilled off in vacuo. Analogously to Example 1f, the residue is treated with HCl/HCOOH, after trituration with ether. After the solvent has been distilled off, the residue is chromatographed analogously to Example 11c. Yield of the chromatographically single peptide: 360 mg. Aminoacid analysis correct.

EXAMPLE 15

H-Tyr-Glu-His-Phe-D-Lys-Phe-NH-(CH$_2$)$_8$-NH$_2$.3CH$_3$COOH

The procedure according to Example 14 is followed, but 565 mg of Boc-Tyr(Bu$^t$)-ONSu are used, and 280 mg of the title compound are obtained.

A single compound in the TLC (C). Aminoacid analysis correct.

EXAMPLE 16

H-Met(O$_2$)-Glu-His-Phe-D-Lys-Phe-NH-(CH$_2$)$_8$-NH$_2$.3HCl (a)

Boc-Met(O$_2$)-Glu(OBu$^t$)-His-Phe-D-Lys(Boc)-Phe-NH-(CH$_2$)$_8$-NH-Boc 0.14 ml of NEM and 150 mg of HOBt are added to 370 mg of Boc-Met(O$_2$)-OH and 1.4 g of H-Glu(OBu$^t$)-HIS-Phe-D-Lys(Boc)-Phe-NH-(CH$_2$)$_8$-NH-Boc. TosOH in 25 ml of DMF. 242 mg of DCC and, after 30 minutes, a further 0.07 ml of NEM are added and, after the mixture has been left to stand overnight, it is worked up. The crude product is dissolved in moist ethyl acetate, the solution is washed with 10% strength KHSO$_4$/K$_2$SO$_4$ solution, saturated sodium bicarbonate solution and water in succession, the ethyl acetate solution is dried briefly over sodium sulfate and concentrated to a small volume and the concentrate is added dropwise to ether, with vigorous stirring. Yield of insoluble crude product: 1.1 g.

(b)

H-Met(O$_2$)-Glu-His-Phe-D-Lys-Phe-NH-(CH$_2$)$_8$-NH$_2$.3CH$_3$COOH

Analogously to Example 11, 650 g of the compound obtained according to (a) are freed from the protective groups and worked up.

Yield: 520 mg.

350 mg are dissolved in 2 ml of 1N acetic acid and the solution is chromatographed on Sephadex ® LH 20 (2.5×100 cm). The main fractions which are a single compound in the TLC are collected and lyophilized.

Yield: 230 mg, a single compound in the TLC (C). Amino-acid analysis correct.

EXAMPLE 17

Z-Glu-Ala-Phe-D-Lys-Phe-NH-(CH$_2$)$_8$-NH$_2$.2HCl (a) Z-Ala-Phe-D-Lys(Boc)-Phe-NH-(CH$_2$)$_8$-NH-Boc 12.7 g of HOBt, 2.84 g of NEM and 4.88 g of DCC are added to 20.85 g of partly protected tripeptide (Example 8b) and 4.95 g of Z-Ala-OH in 300 ml of DMF, with stirring. After the mixture has been left to stand overnight, the DCU is filtered off and the solvent is distilled off in vacuo. The residue is precipitated twice from ethanol/water and the product is dried in vacuo.

Yield: 18.5 g.

[α]$_D^{20}$: −11° (c=1 in 90% strength acetic acid)

C$_{53}$H$_{77}$N$_7$O$_{10}$ (972.3)

Calculated: C 65.47, H 7.98, N 10.09. Found: C 65.6, H 8.0, N 10.3.

(b)

H-Ala-Phe-D-Lys(Boc)-Phe-NH-(CH$_2$)$_8$-NH-Boc.-TosOH 16 g of the Z-compound prepared according to (a) are catalytically hydrogenated on Pd in methanol/DMF, with the addition of 1N TosOH at pH 6. The catalyst is filtered off, the filtrate is clarified with active charcoal, the solvent is distilled off and the residue is triturated with ethyl acetate.

Yield after drying: 12.4 g.

C$_{55}$H$_{84}$N$_8$O$_{12}$ (1081.35).

Calculated: C 61.09, H 7.83, N 10.36, S 2.9. Found: C 60.9, H 7.8, N 10.2, S 3.2.

(c)

Z-Glu-(OBu$^t$)-Ala-Phe-D-Lys(Boc)-Phe-NH-(CH$_2$)$_8$-NH-Boc 2.03 g of Z-Glu(OBu$^t$)-OH are added to 5.0 g of the compound obtained according to (b) in 50 ml of DMF, and 675 mg of HOBt, 0.71 ml of NEM and 1.13 g of DCC are then added, with stirring. After the mixture has been left to stand overnight, the DCU is filtered off, the solvent is distilled off, the residue is taken up n-butanol/ethyl acetate (1:1) and the mixture is washed with sodium bicarbonate solution and water and dried over Na$_2$SO$_4$. The residue which remains after the solvent has been distilled off is digested with ether and dried.

Yield: 5.24 g, a single compound in the TLC (D).

(d) Z-Glu-Ala-Phe-D-Lys-Phe-NH-(CH$_2$)$_6$-NH$_2$.2HCl 300 mg of the compound obtained according to (c) are treated as in Example 1f to split off the protective groups. After working up, the residue is triturated with ether and dried.

Yield: 160 mg.

A single compound in the TLC (D). [α]$_D^{20}$: −15° (c=1, in MeOH).

Aminoacid analysis correct.

EXAMPLE 18

Z-Ala-Phe-D-Lys-Phe-Nh-(CH$_2$)$_8$-NH$_2$.2HCl

Analogously to Example 1f, 1 g of the compound prepared according to Example 17a is treated with formic acid/HCl and the mixture is worked up. Yield: 0.88 g, a single compound in the TLC (A, B).

EXAMPLE 19

H-Met(O$_2$)-Glu-Ala-Phe-D-Lys-Phe-NH-(CH$_2$)$_8$-NH$_2$.3HCl (a)

Boc-Met(O$_2$)-Glu(OBu$^t$)-Ala-Phe-D-Lys(Boc)-Phe-NH-(CH$_2$)$_8$-NH-Boc 344 mg of Boc-Met(O$_2$)-OH, 137 mg of HOBt, 0.13 ml of NEM and 225 mg of DCC are added to 1.2 g of the H-Glu-(OBu$^t$)-Ala-Phe-D-Lys(Boc)-Phe-NH- (CH₂)₈-NH-Boc.TosOH prepared according to Example 21a in DMF, and, after initial stirring, the mixture is left to stand for 15 hours. The mixture is filtered, the solvent is distilled off in vacuo and the residue is triturated with water and ether.

Yield: 1.2 g. The compound still contains a little DCU, but is otherwise a single compound in the TLC (A, d).

(b)

H-Met(O₂)-Glu-Ala-Phe-D-Lys-Phe-NH-(CH₂)₈-NH₂.3HCl

Analogously to Example 1f, the compound prepared according to (a) is treated with formic acid/HCl and the mixture is worked up. The product is then dissolved again in water, the solution is filtered and the filtrate is evaporated to dryness in vacuo. The residue is triturated in ethyl acetate and dried.

Yield from 1.0 g: 0.78 g. A single compound in the TLC (A, B, C).

$[\alpha]_D^{20}$: $-12.5°$ (c=1, methanol).

Aminoacid analysis correct.

EXAMPLE 20

Methylsulfonyl-β-Ala-Glu-Ala-Phe-D-Lys-Phe-NH-(CH₂)₈-NH₂.2HCl (a) Methylsulfonyl-β-alanine 22.3 g of β-alanine are dissolved in 125 ml of 2N MeOH. 20 ml of methanesulfonyl chloride and 145 ml of 2N NaOH are simultaneously added dropwise at 0°–5° C., with vibromixing, and the mixture is vibrated at room temperature for 3 hours. The solution is extracted with ether and the extract is diluted to 400 ml and stirred with a strongly acid ion exchanger (Lewatit ® S 100) until the pH reaches about 2. The solution is then evaporated to dryness in vacuo. The residue is taken up in ethyl acetate, the mixture is dried over sodium sulfate and DCA is added until an alkaline reaction is obtained. The precipitate which separates out is filtered off, washed with ethyl acetate and ether, dried and recrystallized from tetrahydrofuran.

Yield: 17.4 g of DCA salt, melting point: 156°–157°. C₁₆H₃₂N₂O₄S (348.5).

Calculated: C 55.14, H 9.26, N 8.04, S 9.20. Found: C 54.8, H 8.2, N 8.0, S 9.4.

To dissociate the salt, it is dissolved in 200 ml of water and the solution is stirred with a strongly acid ion exchanger until the pH again reaches 2. The solution can also be filtered over a corresponding exchanger column. The solution is evaporated to dryness in vacuo and the residue is dried in a desiccator over P₂O₅ and used in this form. The compound is a single compound in the TLC (A, C).

(b)

CH₃-SO₂-NH-(CH₂)₂-CO-Glu(OBuᵗ)-Ala-Phe-D-Lys(Boc)-Phe-NH-(CH₂)₈-NH-Boc 1.2 g of the Z-peptide obtained according to Example 17c are catalytically hydrogenated according to Example 21a.

Yield: 1.2 g as the tosylate.

The compound is reacted with 204 mg of CH₃SO₂-NH-(CH₂)₂-COOH, 138 mg of HOBt, 0.13 ml of NEM and 225 mg of DCC in 12 ml of DMF and, after the mixture has been left to stand at room temperature for 15 hours, the DCU is filtered off and the solvent is distilled off in vacuo. The residue is triturated with water, filtered off and washed with water and ethyl acetate.

Yield: 1.1 g. A single compound in the TLC (A, D), a little urea still visible.

(c)

CH₃-SO₂-NH-(CH₂)₂-CO-Glu-Ala-Phe-D-Lys-Phe-NH-(CH₂)₈-NH₂.2HCl

Analogously to Example 1f, the protective groups are split off from 0.9 g of the compound obtained according to (b).

Yield: 580 mg. Aminoacid analysis correct.

$[\alpha]_D^{20}$: $-17.6°$ (c=1, methanol).

EXAMPLE 21

Glutaroyl-Glu-Ala-Phe-D-Lys-Phe-NH-(CH₂)₈-NH₂.2HCl (a)

Glutaroyl-Glu(OBuᵗ)-Ala-Phe-D-Lys(Boc)-Phe-NH-(CH₂) -NH-Boc 1.2 g of H-Glu(OBuᵗ)-Ala-Phe-D-Lys(Boc)-Phe-NH-(CH₂)₈-NH-Boc.TosOH, prepared by catalytic hydrogenation of the Z-compound obtained according to Example 17c, are dissolved in 10 ml of pyridine. 140 mg of glutaric anhydride are added and the mixture is left to react at room temperature for 15 hours. The residue which remains after concentration in vacuo is triturated with ethyl acetate and the solid product is filtered off, washed with ether and dried.

Yield: 1.08 g. A single compound in the TLC (A, B, C).

(b)

Glutaroyl-Glu-Ala-Phe-D-Lys-Phe-NH-(CH₂)₈-NH₂.2HCl

Analogously to Example 1f, 0.9 g of the compound obtained according to (a) is treated with formic acid/HCl.

Yield: 0.6 g.

$[\alpha]_D^{20}$: $-19.6°$ (c=1, methanol).

Aminoacid and elementary analysis correct.

The title compound is obtained by dissolving the product in water, treating the solution with a weakly basic ion exchanger to pH 5–6 and concentrating the filtered solution.

EXAMPLE 22

Z-Ala-Ala-Phe-D-Lys-Phe-NH-(CH₂)₈-NH₂.2HCl (a)

Z-Ala-Ala-Phe-D-Lys(Boc)-Phe-NH-(CH₂)₈-NH-Boc 20.85 g of partly protected tripeptide (Example 8b) are reacted with 6.53 g of Z-Ala-Ala-OH, 12.66 g of HOBt, 2.84 ml of NEM and 4.9 g of DCC in 200 ml of DMF, and the mixture is worked up analogously to Example 4a.

Yield: 16.7 g, a single compound in the TLC (C, D).

$[\alpha]_D^{20}$: $-12.0°$ (c=1 in 90% strength acetic acid).

C₅₆H₈₂N₈O₁₁ (1043.3).

Calculated: C 64.47, H 7.92, N 10.74. Found: C 64.2, H 8.0, N 10.6.

(b) Z-Ala-Ala-Phe-D-Lys-Phe-NH-(CH₂)₈-NH₂.2HCl

Analogously to Example 1f, 500 mg of the compound obtained according to (a) are freed from the protective groups. The compound is already a single compound in the TLC (D) without chromatographic purification.

$[\alpha]_D^{20}$: −15.2° (c=1 in 90% strength acetic acid).
$C_{46}H_{68}Cl_2N_8O_7$ (916.0).
Calculated: C 60.32, H 7.98, N 12.23, Cl 7.74. Found: C 60.1, H 7.9, N 12.1, Cl 7.9.
Aminoacid analysis correct.

EXAMPLE 23

H-Glu-Ala-Ala-Phe-D-Lys-Phe-NH-$(CH_2)_8$-$NH_2$.3HCl (a)

H-Ala-Ala-Phe-D-Lys(Boc)-Phe-NH-$(CH_2)_8$-NH-Boc.TosOH

Analogously to Example 17b, 16 g of the compound obtained according to Example 22a are catalytically hydrogenated and the mixture is worked up.
Yield: 12.9 g.
$C_{55}H_{84}N_8O_{12}S$ (1081.35).
Calculated: C 61.09, H 7.83, N 10.36, S 2.96. Found: C 60.9, H 7.8, N 10.2, S 3.2.

(b)

Boc-Gly-Ala-Ala-Phe-D-Lys(Boc)-Phe-NH-$(CH_2)_8$-NH-Boc 973 mg of the compound obtained according to (a) are reacted with 260 mg of Boc-Gly-ONSu in 10 ml of DHF and, after the solvent has been distilled off in vacuo, the title compound is isolated by triturationn with ethyl acetate.
Yield: 850 mg, a single compound in the TLC (D).
$C_{55}H_{87}N_9O_{12}$ (1066.37).
Calculated: C 61.95 H 8.22 N 11.82. Found: C 61.8 H 8.3 N 11.6.

(c)

H-Gly-Ala-Ala-Phe-D-Lys-Phe-NH-$(CH_2)_8$-$NH_2$.3HCl 800 mg of the compound obtained according to (b) are freed from the protective groups analogously to Example 1f.
Yield: 610 mg, a single compound in the TLC (B, D).
$[\alpha]_D^{20}$: −24.0° (c=1, in methanol).
$C_{40}H_{66}Cl_3N_9O_6$ (875.34).
Calculated: C 54.88, H 7.60, N 14.4, Cl 12.5. Found: C 55.0, H 7.5, N 14.2, Cl 12.8.
Aminoacid analysis correct.

EXAMPLE 24

H-Tyr-Ala-Ala-Phe-D-Lys-Phe-NH-$(CH_2)_8$-$NH_2$.3HCl 0.97 g of the compound obtained according to Example 17a is reacted with 435 mg of Boc-Tyr(Bu$^t$)-ONSu in 10 ml of DMF, with the addition of 0.13 ml of NEM. Working up is as in Example 13a. The product (0.8 g) is then freed from the protective groups analogously to Example 1f.
Yield: 0.65 g.
$[\alpha]_D^{20}$: −15.0° (c=1, methanol).
A single compound in the TLC (A, B, C).
Aminoacid analysis correct.

EXAMPLE 25

Glutaroyl-Ala-Ala-Phe-D-Lys-Phe-NH-$(CH_2)_8$-$NH_2$.2HCl

Analogously to Example 21a, the partly protected peptide obtained according to Example 23a is reacted with glutaric anhydride, the protective groups are split off and the mixture is worked up as described.
$[\alpha]_D^{20}$: −19.6° (c=1, methanol)
Aminoacid analysis correct.
The product is dissolved in water and the solution is treated with a weakly basic ion exchanger to pH 5–6 to give the monohydrochloride, which is isolated by concentrating the solution and triturating the residue with ether.

EXAMPLE 26

H-Het($O_2$)-Ala-Ala-Phe-D-Lys-Phe-NH-$(CH_2)_8$-$NH_2$.3HCl

Analogously to Example 16, the title compound is obtained from the peptide prepared according to Example 23a, after splitting off the protective groups.
$[\alpha]_D^{20}$: −15.3° (c=1, methanol).
Aminoacid analysis correct. A single compound in the TLC (A, B, C).

EXAMPLE 27

$CH_3NH$-CO-$(CH_2)_3$-CO-Ala-Ala-Phe-D-Lys-Phe-NH-$(CH_2)_8$-$NH_2$.2HCl (a) Glutaric acid monomethylamide 6.75 g of methylamine.HCl are suspended in 150 ml of DMF and reacted with 11.5 g of glutaric anhydride in the presence of 25.5 ml of NEM. A clear solution is obtained. After the solution has been stirred for 1 hour, it is concentrated in vacuo, 120 ml of acetone are added to the residue and, after filtration, the solvent is distilled off.
The oily residue is extracted with 200 ml+100 ml of ethyl acetate, the ethyl acetate solution is filtered and DCA is added until no further precipitate separates out. The precipitate is recrystallized from isopropanol/ethyl acetate, a first fraction of isopropanol (2 g) being discarded.
Yield: 22 g.
$C_{18}H_{34}N_2O_3$ (326.5).
Calculated: C 66.22, H 10.50, N 8.58. Found: C 65.7, H 10.3, H 8.5.
The salt is dissociated analogously to Example 20a.
Yield: 7.9 g of oil, chromatographically pure.

(b)

$CH_3NH$-CO-$(CH_2)_3$-CO-Ala-Ala-Phe-D-Lys-Phe-NH-$(CH_2)$-$NH_2$.2HCl 121 mg of HOBt, 0.12 ml of NEM and 200 mg of DCC are added in succession with stirring to 15 g of the compound prepared according to (a) and 975 mg of H-Ala-Ala-Phe-D-Lys(Boc)-Phe-NH-$(CH_2)_8$-NH-Boc.TosOH, prepared according to Example 23a, in 8 ml of DMF, and the mixture is left to stand at room temperature for 15 hours. Working up is carried out analogously to Example 17c. TLC (A): a single compound. Yield: 923 mg. The protective groups are split off analogously to Example 1f.
Yield: 790 mg. Elementary analysis correct.

EXAMPLE 28

$CH_3NH$-CO-$(CH_2)_3$-CO-Glu-Ala-Phe-D-Lys-Phe-NH-$(CH_2)_8$-$NH_2$.2HCL

The procedure followed is analogous to Example 27b, but an equimolar amount of H-Glu(OBu$^t$)-Ala-Phe-D-Lys(Boc)-Phe-NH-$(CH_2)_8$-NH-Boc.TosOH, prepared according to Example 20b, is employed. In the

EXAMPLE 29

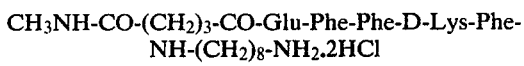

The procedure followed is analogous to Example 27b, but an equimolar amount of H-Glu(OBu$^t$)-Phe-Phe-D-Lys(Boc)-Phe-NH-(CH$_2$)$_8$-NH-Boc.TosOH, prepared according to Example 34d, is employed.

EXAMPLE 30

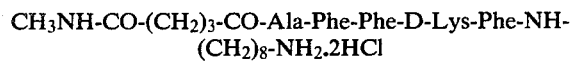

The procedure followed is analogous to Example 27b, but the equimolar amount of H-Ala-Phe-Phe-D-Lys(Boc)-Phe-NH-(CH$_2$)$_8$-NH-Boc.TosOH, prepared according to Example 37, is employed.

EXAMPLE 31

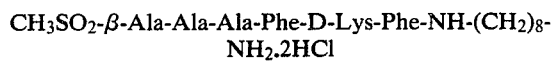

975 mg of the partly protected peptide prepared according to Example 23a are reacted with 180 mg of methylsulfonyl-β-alanine analogously to Example 27b, the protective groups are split off as described and the mixture is worked up.

Yield: 540 mg. $[\alpha]_D^{20}$: −18.5° (c=1, in methanol). Aminoacid analysis correct. A single compound in the TLC (A).

EXAMPLE 32

Acetylaminocaproyl-Ala-Phe-D-Lys-Phe-NH-(CH$_2$)hd 8-NH$_2$.2HCl (a) Acetylaminocaproic acid hydroxysuccinimide ester 26.2 g of ε-aminocaproic acid are suspended in 100 ml of acetic acid. 22.2 ml of acetic anhydride are added and the mixture is stirred at room temperature for 5 hours. The clear solution is evaporated to dryness in vacuo and the residue is digested with ether, filtered off, washed with ether and dried in vacuo.

Yield: 30.4 g. C$_8$H$_{15}$NO$_3$. Calculated: C 55.47, H 8.73, N 8.09. Found: C 55.4, H 8.8, N 8.0.

8.3 g of N-hydroxysuccinimide and 13.2 g of DCC are added to 10.4 g in 150 ml of acetonitrile. The mixture is left to stand overnight, the DCU is filtered off and the solvent is distilled off in vacuo. The residue is digested with petroleum ether and diisopropyl ether and dried.

Yield: 16.9 g. This product is used without further purification for the reaction.

(b)
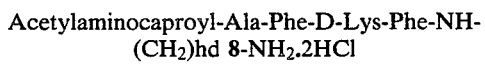

1 g of H-Ala-Phe-D-Lys(Boc)-Phe-NH-(CH$_2$)$_3$-NH-Boc.TosOH, prepared according to Example 17b, in 8 ml of DMF is reacted with 0.3 g of the active ester prepared according to (a), with the addition of 0.5 ml of NEM, the mixture is left to stand overnight and the solvent is distilled off in vacuo. The residue is digested with ethyl acetate and water, filtered off and washed with ethyl acetate and ether.

Yield after drying: 0.9 g. A single compound in the TLC (A). Elementary analysis correct. The splitting off of the protective groups and working up are carried out analogously to Example 1f.

$[\alpha]_D^{20}$: −18.2° (c=1, in methanol).

EXAMPLE 33

(a) Methylsulfonyl-ε-aminocaproic acid

Analogously to Example 20a, 65.6 g of ε-aminocaproic acid are reacted with 40 ml of methanesulfonyl chloride in the presence of 2N NaOH and the mixture is worked up. The DCA salt is prepared, and 42.3 g of melting point 134° are obtained.

C$_{19}$H$_{38}$N$_2$O$_4$S (390.6).

Calculated: C 58.43, H 8.81, N 7.17, S 8.21. Found: C 58.2, H 9.9, N 7.4, S 8.4.

The acid is liberated according to Example 20a.

Yield: 24.6 1 g of oil, which crystallizes completely. Pure in the TLC (A, B, C).

(b)
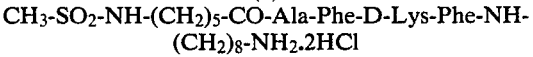

Analogously to Example 20, 975 mg of the partly protected peptide obtained according to Example 17b are reacted with 225 mg of the compound obtained according to (a) to give, after splitting off of the protective groups and corresponding working up, 724 mg of the title compound. Aminoacid analysis correct, almost a single compound in the TLC (A, B).

EXAMPLE 34

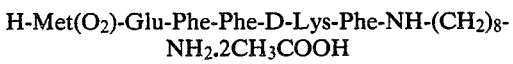

(a) Z-Phe-Phe-D-Lys(Boc)-Phe-NH-(CH$_2$)$_8$-NH-Boc 3.9 g of Z-Phe-OH and 12.2 g of H-Phe-D-Lys(Boc)-Phe-NH-(CH$_2$)$_8$-NH-Boc.TosOH, prepared according to Example 9a, are reacted with 1.7 ml of NEM, 1.76 g of HOBt and 2.9 g of DCC in 150 ml of DMF in the manner described above. After the mixture has been left to stand at room temperature for 15 hours, the DCU is filtered off, the solution is evaporated to dryness in vacuo and the residue is recrystallized from ethanol.

Yield: 8.1 g, not quite a single compound in the TLC (A, B, C), but the aminoacid analysis is correct in the context of the limits of error.

(b)
H-Phe-Phe-D-Lys(Boc)-Phe-NH-(CH$_2$)$_8$-NH-Boc.-TosOH 7.2 g of the title compound are obtained from 8.0 g of the compound prepared according to (a), after catalytic hydrogenation analogously to Example 7b, and the product is used in this form as a chromatographically almost pure starting compound for the following stage.

(c)
Z-Glu(OBu$^t$)-Phe-Phe-D-Lys(Bo)-Phe-NH-(CH$_2$)$_8$-NH-Boc 4.0 g of Z-Glu(OBu$^t$)-OTcp and 7.6 g of the compound obtained according to (b) are kept in the presence of 0.9 ml of NEM and 100 ml of DMF for 15 hours. After the solvent has been distilled off in vacuo, the residue is redissolved from isopropanol.

Yield: 9.0 g. Almost a single compound in the TLC (A, B).

Aminoacid analysis correct.

(d)
H-Glu(OBu')-Phe-Phe-D-Lys(Boc)-Phe-NH-(CH₂)₈-NH-Boc.TosOH 4.8 g of product which, in the TLC (A, B) is a single compound, are obtained by catalytic hydrogenation of the compound obtained according to (c) analogously to (b) after digestion with ether and water, drying and reprecipitation from ethanol/ether.

(e)
Boc-Met(O₂)-Glu(OBu')-Phe-Phe-D-Lys(Boc)-Phe-NH-(CH₂)₈NH-Boc 2.54 g of the compound obtained according to (d) in 50 ml of DMF and in the presence of 0.26 ml of NEM, 270 mg of HOBt and 440 mg of DCC are reacted with 675 mg of Boc-Met(O₂)-OH analogously to Example 16a and the mixure is worked up as described in that example.

Yield: 2.2 g, almost a single compound in the TLC (A, B, C).

(f)
H-Met(O₂)-Glu-Phe-Phe-D-Lys-Phe-NH-(CH₂)₈-NH₂2CH₃COOH 1.9 g of the compound obtained according to (c) are freed from the protective groups analogously to Example 1f and, analogously to Example 11c, the reaction product is converted into the acetate and the acetate is purified by chromatography. After reprecipitation from methanol/ethyl acetate, 0.6 g of chromatographically pure (A, B, C) peptide with a correct aminoacid analysis is obtained.

EXAMPLE 35

H-Met(O₂)-D-Glu-Phe-Phe-D-Lys-Phe-NH-(CH₂)₈-NH₂.2CH₃COOH

The procedure followed is as described under Example 34, but Z-D-Glu(OBu')-OTcp is used.

EXAMPLE 36 pGlu-His-Phe-D-Lys-phe-NH-(CH₂)₈-NH₂.2CH₃COOH (a)
pGlu-His-Phe-D-Lys(Boc)-Phe-NH-(CH₂)₈-NH-Boc 0.8 g of pGlu-His-OH and 2.8 g of H-Phe-D-Lys(-Boc)-Phe-NH-(CH₂)₈-NH-8oc, prepared according to Example 9a, are dissolved in 50 ml of DMF. 490 mg of HOObt, 0.4 ml of NEM and 660 mg of DCC are added in succession and the mixture is stirred at room temperature for 15 hours. The residue which remains after filtering off the DCU and distilling off the solvent is digested with saturated sodium bicarbonate solution and water and reprecipitated from methanol/ethyl acetate.

Yield: 1.6 g, almost chromatographically pure (A, C).

(b)
pGlu-His-Phe-D-Lys-Phe-NH-(C₂)₈-NH₂.2CH₃COOH

The splitting off of the protective groups, conversion into the acetate and chromatographic purification are carried out analogously to Example 11c.

Yield: 0.78 g. A single compound in the TLC (A, C), aminoacid analysis correct.

EXAMPLE 37

H-Met(O₂)-Ala-Phe-Phe-D-Lys-Phe-NH-(CH₂)₈-NH₂.2CH₃COOH

The procedure followed is as described in Example 34, but instead of Z-Glu(OBu')-OTpc, the equimolar amount of Z-Ala-OTcp is employed to give, after splitting off of the protective groups analogously to 1f, conversion into the acetate and chromatography analogously to Example 11c, the title compound in chromatographically pure form with a correct aminoacid analysis.

EXAMPLE 38

H-Met(O₂)-Ala-Ala-Ala-D-Lys-Phe-NH-(CH₂)₈-NH₂.3HCl (a) H-Ala-D-Lys(Boc)-Phe-NH-(CH₂)₈-NH-BOC.HCl

The procedure followed is as described in Example 8a, but the Z-Phe-OH is replaced by 3.1 g of Z-Ala-OH. 7.5 g of Z-Ala-D-Lys(Boc)-Phe-NH-(C₂)₈-NH-Boc are obtained, from which the Z group is split off analogously to 8b. A single compound in the TLC (C, D), aminoacid analysis correct.

(b)
H-Met(O₂)-Ala-Ala-Ala-D-Lys-Phe-NH-(CH₂)₈-NH₂.3HCl

The compound obtained according to (a) is first reacted with Z-Ala-Ala-OH, DCC and HOBt analogously to Example 22a, the Z group is split off by catalytic hydrogenation as described above, the product is reacted with Boc-Met(O₂)-OH, DCC and HOBt analogously to Example 16a, and the protective groups are split off analogously to Example 1f. The title compound is almost a single compound in the TLC (A, B), aminoacid analysis correct.

EXAMPLE 39

H-Met(O₂)-Ala-Ala-Leu-D-Lys-phe-NH-(CH₂)₈-NH₂.3HCl

The procedure followed is as described in Example 38a, but 3.7 g of Z-Leu-OH are employed and the subsequent procedure is as described in 38b. The title compound is almost a single compound in the TLC (A) and shows the correct aminoacid analysis.

EXAMPLE 40

Z-D-Lys-Phen-NH-(CH₂)₉-NH₂.2HCl (a) Z-D-Lys(Boc)-Phe-NH-(CH₂)₉-NH-Boc

Analogously to Example 1c, 27 g of NH₂-(CH₂)₉-NH-Boc.HCl, prepared analogously to Example 1a-b, are reacted with 48 g of Z-D-Lys-Phe-OH and the mixture is worked up.

Yield: 81.7 g. $[\alpha]_D^{20}$: +1.9° (c=1, in methanol). C₄₂H₆₄N₅O₈ (767.0). Calculated: C 65.77, H 8.41, N 9.13. Found: C 65.2, H 8.5, N 9.0.

(b) Z-D-Lys-Phe-NH-(CH₂)₉-NH₂.2HCl

The title compound is obtained in the form of a chromatographically single compound (A, B) by splitting off the protective groups from a compound obtained according to (a) analogously to Example 1f. Elementary analysis correct.

EXAMPLE 41

H-Met($O_2$)-Glu-His-Phe-D-Lys-Phe-NH-($CH_2$)$_9$-$NH_2$.3$CH_3$COOH

The Z group is split off from the peptide derivative obtained according to Example 40a analogously to Example 8a and the product is then reacted with Z-Phe-OH as described in that example. The Z group is then split off analogously to Example 8b and the further procedure is as described in Examples 9b and 16a. The protected title compound is obtained, from which the protective groups are split off according to Example 1f. Working up and purification are carried out according to Example 11c. Aminoacid analysis correct.

EXAMPLE 42

H-Met($O_2$)-Glu-His-Phe-D-Lys-Phe-NH-($CH_2$)$_{10}$-$NH_2$.3$CH_3$COOH

The procedure followed is as described in Examples 40a and 41, but $NH_2$-($CH_2$)$_{10}$-NH-Boc.HCl is employed in the first step.

After purification analogously to Example 11c, the title compound is chromatographically a single compound and exhibits a correct aminoacid analysis.

EXAMPLE 43

H-Met($O_2$)-Glu-His-Phe-D-Lys-Phe-NH-($CH_2$)$_6$-$NH_2$.3$CH_3$COOH

The procedure followed is analogous to Example 42, but $NH_2$-($CH_2$)$_6$-NH-Boc.HCl is employed as a basic radical.

EXAMPLE 44

H-Met($O_2$)-Glu-His-Phe-D-Lys-Gly-NH-($CH_2$)$_2$-$NH_2$.3$CH_3$COOH (a) Z-D-Lys(Boc)-Phe-Gly-NH-($CH_2$)$_2$-NH-Boc

According to Example 7d, Z-D-Lys(Boc)-Phe-GlyOMe, prepared according to Example 7a, is subjected to alkaline hydrolysis and the mixture is correspondingly worked up. Reaction with $NH_2$-($CH_2$)$_2$-NH-Boc.HCl analogously to Example 1e leads to the title compound.

$C_{37}H_{53}N_6O_9$ (725.9).

Calculated: C 61.22, H 7.36, N 11.58. Found: C 60.8, H 7.5, N 11.3.

(b) H-Met($O_2$)-Glu-His-Phe-D-Lys-Phe-Gly-NH-($CH_2$)$_2$-$NH_2$.3$CH_3$COOH

The Z protective group is split off from the compound obtained according to (a) analogously to Example 41 and the subsequent procedure is as described under Example 41. After purification analogously to Example 11c, the title compound is a single compound in the TLC (A, C) and exhibits a correct aminoacid analysis.

EXAMPLE 45

H-Met($O_2$)-Glu-His-Phe-D-Lys-Phe-Gly-NH-($CH_2$)$_6$-$NH_2$.3$CH_3$COOH

The procedure followed is analogous to Example 44, but $NH_2$-($CH_2$)$_6$-NH-Boc.HCl is employed as the basic amide.

EXAMPLE 46

Phenylpropionyl-Ala-Ala-Phe-D-Lys-Phe-NH-($CH_2$)$_8$-$NH_2$.2HCl 970 mg of the partly protected peptide obtained according to Example 23a, are reacted with 150 mg of phenylpropionic acid analogously to Example 10 to give, after the protective groups have been split off analogously to Example 1f, 630 mg of the title compound.

$[\alpha]_D^{20}$: −18.0° (c=1, in methanol).

A single compound in the TLC in B and D.

EXAMPLE 47

Phenylpropionyl-D-Lys-Phe-NH-($C_2$)$_8$-$NH_2$.2HCl (a) Phenylpropionyl-D-Lys(Boc)-Phe-NH-($CH_2$)$_8$-NH-Boc 7.5 g of Z-D-Lys(Boc)-Phe-NH-($CH_2$)$_8$-NH-Boc, prepared according to Example 1e, are catalytically hydrogenated analogously to Example 8a and, analogously to Example 10, the product is reacted with 1.5 g of phenylpropionic acid and the mixture is worked up.

Yield: 7.9 g. $[\alpha]_D^{20}$: +3.2° (c=1, in methanol). $C_{51}H_{73}N_6O_8$ (898.2). Calculated: C 68.21, H 8.19, N 9.36. Found: C 68.0, H 8.2, N 9.2.

(b) Phenylpropionyl-D-Lys-Phe-NH-($CH_2$)$_8$-$NH_2$.2HCl

Analogously to Example 1f, the compound obtained according to (a) is freed from the protective groups and worked up.

Yield: 7.1 g, a single compound in the TLC (A, B).

EXAMPLE 48

Z-D-Lys-($CH_3$)-Phe-NH-($CH_2$)$_8$-$NH_2$.2HCl (a) Z-D-Lys(Boc)-($CH_3$)-Phe-$OCH_3$

Analogously to Example 1c, 38 g of Z-Lys(Boc)-OH are reacted with 23 g of N-methyl-L-phenylalanine methyl ester hydrochloride in 500 ml of DMF in the presence of 12.8 ml of NEM and 13.5 g of HOBt with 22 g of DCC at room temperature. After filtration and removal of the solvent by distillation in vacuo, the residue is taken up in ethyl acetate and the mixture is washed with 10% strength $KHSO_4/K_2SO_4$, sodium bicarbonate solution and water. After the solution has been dried over $Na_2SO_4$, the ethyl acetate has been distilled off and the residue has been digested, 48.2 g of the title compound are obtained.

Calculated: C 64.85, H 7.44, N 7.56. Found: C 65.0, H 7.3, N 7.5.

(b) Z-D-Lys-($CH_3$)Phe-NH-($CH_2$)$_8$-$NH_2$.2HCl

The compound obtained according to (a) is hydrolyzed analogously to Example 1d, the resulting dipeptide acid is reacted with the Boc-diamine analogously to Example 1e and the Boc groups are split off according to Example 1f. Elementary analysis correct. A single compound in the TLC (A, B).

EXAMPLE 49

H-Met($O_2$)-Glu-His-Phe-D-Lys-Phe-Gly-D-Lys-pyrrolidide.3$CH_3$COOH

Analogously to Example 1e, Z-D-Lys(Boc)-Phe-Gly-OH, prepared according to Example 44a, is reacted with H-D-Lys(Boc)-pyrrolidide, which is obtained by catalytic hydrogenation of the Z compound. The subsequent procedure is as described in Example 44b, to give the title compound with a correct aminoacid analysis.

EXAMPLE 50

H-Met(O$_2$)-Glu-His-Phe-D-Lys-Phe-Gly-Lys-diethylamide.3CH$_3$COOH

The procedure followed is analogous to Example 49, but H-Lys(Boc)-diethylamide is employed. The title compound purified according to Example 11c is a single compound in the TLC (A, B) and exhibits a correct aminoacid analysis.

EXAMPLE 51

CH$_3$CO-β-Ala-Ala-Ala-Phe-D-Lys-Phe-NH-(CH$_2$)$_8$-NH$_2$.2HCl

The procedure followed is analogous to Example 31, but the amount of acetyl-β-aniline equivalent to the partly protected peptide prepared according to Example 23a is employed. The title compound is obtained, with a correct aminoacid analysis.

EXAMPLE 52

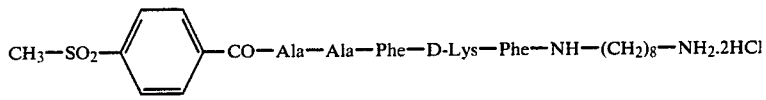
CH$_3$—SO$_2$— [phenyl] —CO—Ala—Ala—Phe—D-Lys—Phe—NH—(CH$_2$)$_8$—NH$_2$.2HCl The procedure followed is analogous to Examples 31 and 51, but 4-methylsulfonylbenzoic acid is used as the reactant. S:N ratio correct.

We claim:

1. A pharmaceutical composition comprising an effective amount of a compound of the general formula I

R$^4$-A$^5$-A$^6$-R$^7$  (I)

in which:
R$^4$ denotes benzyloxycarbonyl (Z), (C$_2$-C$_6$)-alkanoyl, (C$_6$-C$_{10}$)-aryl-(C$_2$-C$_4$)-alkanoyl or cycloalkanoyl with up to 2 alkyl and 5-7 cycloalkyl carbon atoms, bonded via Nα, or
R$^3$-A$^4$, in which
A$^4$ is selected from the group consisting of Ala, Val, Leu, Ile, Met, Ser(C$_1$-C$_6$-alkyl), Thr (C$_1$-C$_6$-alkyl), Cys(C$_1$-C$_6$-alkyl), Phe, C-phenylgycine and Tyr(C$_1$-C$_6$-alkyl) and
R$^3$ represents hydrogen, Z, (C$_2$-C$_6$)-alkanoyl, (C$_6$-C$_{10}$)-aryl-(C$_2$-C$_4$)-alkanoyl or cycloalkanoyl with up to 2 alkyl and 5-7 cycloalkyl carbon atoms, bonded via Hα, or
R$^2$-A$^3$-A$^4$, in which
A$^4$ is as defined above,
A$^3$ denotes His, Ala, Phe or D-Lys and
R$^2$ is defined as R$^3$, or represents (C$_2$-C$_4$)-alkanoyl-ω-amino-(C$_5$-C$_8$)-n-alkanoyl, methylsulfonyl-ω-amino-(C$_5$-C$_8$)-n-alkanoyl, 4-methylsulfonylbenzoyl, succinoyl or glutaroyl, bonded via Hα, or
R$^1$-A$^2$-A$^3$-A$^4$, in which
A$^3$ and A$^4$, are as defined above,
A$^2$ represents pyroglutamyl, Glu, D-Glu or Ala and
R$^1$ is defined as R$^2$, or represents (C$_2$-C$_4$)-alkanoyl-ω-amino-C$_3$-C$_4$)-n-alkanoyl, methylsulfonyl-ω-amino-(C$_3$-C$_4$)-n-alkanoyl, methylamido-glutaroyl, H-Met, H-D-Met, H-Met(O), H-D-Met(O), H-Met(O$_2$), H-D-Met (O$_2$), H-Gly, Z-Gly, H-Tyr, Z-Tyr or pyroglutamyl, bonded via Nα,
A$^5$ denotes D-Lys or Lys,
A$^6$ denotes the radical of phenylalanine, N-methylphenylalanine, 4-(C$_1$-C$_4$)-alkoxyphenylalanine or 1,2,3,4-tetrahydroisoquinoline-3-carboxylic acid and
R$^7$ denotes NH-(CH$_2$)$_n$-NH$_2$, Gly-NH-(CH$_2$)$_m$-NH$_2$, Gly-Lys-R$^8$ or Gly-D-Lys-R$^8$, in which n represents an integer from 4 to 10, m represents a integer from 2 to 6 and R$^8$ represents 1-pyrrolidinyl, 1-piperidinyl, NH-R or NR$_2$, where R=(C$_1$-C$_4$)-alkyl, or one of its physiological acceptable salts, and a physiological acceptable carrier.

2. A method of improving learning and memory performance, by administration of a pharmaceutical composition as claimed in claim 1.

3. A method of treating post-traumatic and degenerative brain damage by adminsitering a pharmaceutical composition as claimed in claim 2.

4. A pharmaceutical composition having mood-lightening, antidepressant and anxiolytic properties comprising a pharmaceutically effective amount of a compound as claimed in claim 1.

* * * * *